United States Patent
McIntyre et al.

(10) Patent No.: US 6,168,652 B1
(45) Date of Patent: Jan. 2, 2001

(54) PROCESS FOR PURIFYING HALOSILANES

(75) Inventors: Michael Andrew McIntyre, Midland, MI (US); Oliver K. Wilding, Lagrange, KY (US)

(73) Assignee: Dow Corning Corporation, Midland, MI (US)

(*) Notice: Under 35 U.S.C. 154(b), the term of this patent shall be extended for 582 days.

(21) Appl. No.: 08/553,733

(22) Filed: Oct. 23, 1995

(51) Int. Cl.⁷ .................................. B01D 53/04
(52) U.S. Cl. ........................ 95/143; 95/144; 95/148; 210/670; 210/691
(58) Field of Search ................. 95/143–147; 210/670, 210/690, 691

(56) References Cited

U.S. PATENT DOCUMENTS

| | | | |
|---|---|---|---|
| 1,382,889 | * | 6/1921 | Burrell et al. .................. 95/147 X |
| 1,453,215 | * | 4/1923 | Voress et al. ...................... 95/147 |
| 1,742,247 | * | 1/1930 | Godel ............................ 95/147 X |
| 2,380,995 | | 8/1945 | Rochow ............................ 260/607 |
| 2,395,491 | * | 2/1946 | Mavity ........................ 210/690 X |
| 2,780,358 | * | 2/1957 | Mosesman et al. ............. 210/690 X |
| 2,782,869 | * | 2/1957 | Gray ............................... 95/147 |
| 4,056,369 | | 11/1977 | Quackenbush ...................... 55/58 |
| 4,066,423 | | 1/1978 | McGill et al. ...................... 55/48 |
| 4,151,078 | * | 4/1979 | Calvin ......................... 210/690 X |
| 4,338,101 | | 7/1982 | Tuttle .............................. 55/48 |
| 4,344,841 | * | 8/1982 | Johnson et al. ................ 210/690 X |
| 4,421,532 | | 12/1983 | Sacchetti et al. ..................... 55/28 |
| 4,462,811 | | 7/1984 | Dinsmore et al. ..................... 55/18 |
| 5,051,117 | * | 9/1991 | Prigge et al. ................... 95/143 X |
| 5,206,004 | * | 4/1993 | Park ............................ 95/144 X |
| 5,290,342 | * | 3/1994 | Wikman et al. .................... 95/143 |
| 5,294,246 | * | 3/1994 | Gardner, Sr. ................... 95/146 X |
| 5,393,329 | * | 2/1995 | Inagaki et al. ................. 95/146 X |
| 5,445,742 | | 8/1995 | Bothe Almquist et al. ......... 210/670 |
| 5,536,301 | * | 7/1996 | Lansbarkis et al. ............. 95/147 X |

FOREIGN PATENT DOCUMENTS

| | | | | |
|---|---|---|---|---|
| 0652599 | * | 11/1962 | (CA) | ...................... 95/143 |
| 2461759 | * | 9/1975 | (DE) | ...................... 95/143 |
| 0296301 | * | 7/1928 | (GB) | ..................... 210/690 |
| 0719832 | * | 12/1954 | (GB) | ..................... 210/690 |
| 53-057240 | * | 5/1978 | (JP) | ...................... 95/147 |
| 0806080 | * | 2/1981 | (SU) | ...................... 95/147 |
| 1011502 | * | 4/1983 | (SU) | ...................... 95/143 |

* cited by examiner

*Primary Examiner*—Robert H. Spitzer
(74) *Attorney, Agent, or Firm*—William F. Boley

(57) ABSTRACT

A process for purifying halosilanes consisting of contacting a mixture comprising a halosilane and a hydrocarbon with silica gel, thereby reducing the hydrocarbon content of the mixture. The present process is particularly useful for removing hydrocarbon contaminates from chlorosilanes, where the hydrocarbon contaminates have a boiling point similar to that of the chlorosilanes.

17 Claims, No Drawings

PROCESS FOR PURIFYING HALOSILANES

BACKGROUND OF INVENTION

The present invention is a process for the purification of halosilanes. The process consists of contacting a mixture comprising a halosilane and a hydrocarbon with silica gel, thereby reducing the hydrocarbon content of the mixture. The present process is particularly useful for removing hydrocarbon contaminates from chlorosilanes, where the hydrocarbon contaminates have a boiling point similar to that of the chlorosilanes.

Hydrocarbon contaminates in halosilanes can create quality problems such as undesirable odor and color not only in the halosilanes, but in products made from the halosilanes. In addition, in cyclic processes using halosilanes as feed, where unreacted materials are being recovered and fed back to the process, hydrocarbons can build up in the process leading to a decrease in process capacity and operational control. Often it is hard to remove these hydrocarbon contaminates from the halosilanes by standard processes such as distillation because of similar boiling points.

The present process is particularly useful for removing hydrocarbon contaminates from halosilanes prepared by the reaction of an organohalide with silicon metalloid in the presence of a suitable catalyst, as was originally described by Rochow, U.S. Pat. No. 2,380,995, issued Aug. 7, 1945.

The use of adsorbents to recover hydrocarbons from air and hydrocarbon mixtures generated during the production and transfer of petroleum products is described, for example, in Quackenbush, U.S. Pat. No. 4,056,369, issued Nov. 1, 1977; McGill et al., U.S. Pat. No. 4,066,423, issued Jan. 3, 1978; Dinsmore et al., U.S. Pat. No. 4,462,811, issued Jul. 31, 1984; and Tuttle, U.S. Pat. No. 4,338,101, issued Jul. 6, 1982. A typical adsorbent used to recover the hydrocarbons is activated carbon.

Sacchetti et al., U.S. Pat. No. 4,421,532, issued Dec. 20, 1983, describe a process for recovering volatile organic substances from industrial waste gases. The process involves the passing of the waste gas through a bed of an adsorbent such as activated carbon, silica gel, alumina, or molecular sieve to remove volatile organic substances, and then regenerating the adsorbent bed by stripping with steam or a hot gas.

Bothe et al., U.S. Pat. No. 5,445,742, issued Aug. 29, 1995, describe a process for purification of halosilanes. The process consists of contacting a mixture comprising a halosilane and a hydrocarbon with an adsorbent selective for the hydrocarbon. Bothe et al. teach that the adsorbent is characterized by being (1) hydrophobic and (2) organophilic and by having (3) a neutral surface, and (4) no polarizable pendant groups. Examples of useful adsorbents taught by Bothe et al. are activated carbon, carbon molecular sieves, and high silica zeolites.

The present inventors have found that hydrocarbon contaminates present in halosilane liquids and gases can be reduced by contacting the halosilane liquid or gas with silica gel. The described art does not recognize that silica gel can selectively adsorb hydrocarbon contaminates from halosilane liquids and gases.

SUMMARY OF INVENTION

The present invention is a process for purifying halosilanes. The process consists of contacting a mixture comprising a halosilane and a hydrocarbon with silica gel, thereby reducing the hydrocarbon content of the mixture. The present process is particularly useful for removing hydrocarbon contaminates from chlorosilanes, where the hydrocarbon contaminates have a boiling point similar to that of the chlorosilanes.

DESCRIPTION OF INVENTION

The present invention is a process for reducing hydrocarbon content of halosilanes. The process comprises contacting a mixture comprising a halosilane and a hydrocarbon with silica gel, thereby reducing the hydrocarbon content of the mixture.

Preferred halosilanes from which hydrocarbons can be adsorbed are described by formula $R_aH_bSiX_{4-a-b}$, where a=0 to 3, b=0 to 3, a+b=0 to 3, X is a halogen, and R is a monovalent hydrocarbon radical comprising about one to 12 carbon atoms. The preferred halogen, X, is chlorine. R can be, for example, methyl, ethyl, propyl, tert-butyl, vinyl, allyl, and phenyl.

The halosilane can be, for example, trimethylchlorosilane, dimethyldichlorosilane, methyltrichlorosilane, dimethylchlorosilane, phenylmethyldichlorosilane, phenyltrichlorosilane, trichlorosilane, tetrachlorosilane, methylvinyldichlorosilane, and dimethyldivinylchlorosilane. The present process is particularly useful for removing hydrocarbon contaminates from methylchlorosilane mixtures comprising dimethyldichlorosilane and methyltrichorosilane.

Hydrocarbons which can be removed by the present process are those which are typically found in trace amounts in halosilanes after distillation processes. The specific types of hydrocarbons present in the halosilanes will depend upon the particular halosilane and its separation history. For purposes of this invention the term "hydrocarbons" includes saturated hydrocarbons, unsaturated hydrocarbons, and halogenated hydrocarbons. The present process is especially useful for removing those hydrocarbons having boiling points similar to the halosilane of interest, where the hydrocarbons cannot readily be separated by distillation. The present process is especially useful for removing hydrocarbons comprising about one to 12 carbon atoms from chlorosilanes.

The mixture comprising a halosilane and a hydrocarbon is contacted with silica gel, thereby reducing the hydrocarbon content of the mixture. Silica gels useful in the present process can be of the regular-density, intermediate-density, or low-density types. Such silica gels are described, for example, in Kirk-Othmer, Encyclopedia of Chemical Technology, Vol. 20, Third Edition, p. 773–774, John Whiley & Sons, NY, 1982. It is preferred that the silica gel have a surface area of at least about 200 $m^2/g$. More preferred is when the silica gel is of the regular-density type and has a surface area greater than about 500 $m^2/g$. A preferred silica gel is one which contains about 0.1 to 10 weight percent alumina ($Al_2O_3$). Even more preferred is when the silica gel contains about one to five weight percent alumina.

Since chlorosilanes readily hydrolyze on contact with water, it may be necessary to at least partially dry the silica gel prior to use. Drying of the silica gel can be effected by standard methods known in the art such as by heating under reduced pressure. An example of a useful method for drying the silica gel is described in the examples herein.

The mixture comprising a halosilane and a hydrocarbon can be contacted with the silica gel by standard methods for contacting a gas or liquid halosilane with a solid. The process can be run as a batch, semi-continuous, or continuous process. Preferred is when the mixture comprising a halosilane and a hydrocarbon is a liquid when contacted with the silica gel.

In one embodiment of the present process, once the silica gel becomes saturated with hydrocarbon and breakthrough occurs, the silica gel may be desorbed and reused in the process. The process may be run as a continuous process using multiple beds of silica gel, where adsorption and desorption of the beds is staged to provide a continuous process. Adsorption and desorption of the silica gel can be accomplished by standard methods such as a pressure swing adsorption and desorption process, a temperature swing adsorption and desorption process, or a combination of pressure and temperature swing adsorption and desorption processes. The method of desorption of the silica gel is not critical to the present process and may be any of those methods known in the art for desorbing adsorbents.

The length of time the mixture containing halosilane and hydrocarbon is in contact with the silica gel will depend upon the particular silica gel used, the hydrocarbon to be adsorbed, and the concentration of hydrocarbon. Examples of useful contact times are provided in the examples herein. Generally, any contact time sufficient for any or all of the hydrocarbon to be adsorbed from the mixture is considered useful.

The following examples are provided to illustrate the present invention. These examples are not intended to limit the scope of the present claims.

EXAMPLES

A number of silica gels were evaluated for their ability to adsorb hydrocarbon contaminates from a methylchlorosilane mixture. The silica gels tested were products of Engelhard, Charlotte, N.C. The manufacturer's designation for each of the silica gels along with typical physical properties is provided in Table 1.

TABLE 1

Silica Gels Tested

| Name | Surface Area ($m^2/g$) | Pore Vol. (cc/g) | Ave. Pore Size (Angstrom) | Alumina (Wt. %) |
|---|---|---|---|---|
| Sorbead WS | 650 | 0.40 | 25 | 3 |
| Sorbead H | 750 | 0.47 | 25 | 3 |
| Sorbead R | 750 | 0.35 | 20 | 3 |
| Sorbead W | 275 | 0.30 | — | 10 |
| Sorbead AF | 700 | 0.40 | 25 | 0.3 |
| Sorbead AC | 750 | 0.60 | — | — |

Fifteen to 20 grams of a silica gel was placed in a 50 ml flask. The flask was heated at about 350° C. under vacuum at 30 mm Hg for six to eight hours to dry. The flask was cooled and purged with dry nitrogen. Thirty grams of a chlorosilane mixture comprising methyltrichlorosilane, 12,000 ppm dimethyldichlorosilane, and hydrocarbon contaminates as described in Table 2 were injected into the cooled flask through a rubber septum. The concentrations of hydrocarbon contaminates given in Table 2 are average values for the methylchlorosilane stream from which the methylchlorosilane mixture was sampled.

TABLE 2

Hydrocarbon Contaminates

| Hydrocarbon | ppm |
|---|---|
| Trans-2-hexene | 7 |
| 2-Methyl-2-pentene | 6 |
| Cis-3-methyl-2-pentene | 20 |
| Trans-3-methyl-2-pentene | 50 |
| 2,3-Dimethyl-2-butene | 85 |
| 2-Chloro-2-methylpentane | 5 |
| 2-Chloro-2,3-dimethylbutane | 30 |
| 3-Chloro-3-methylpentane | 30 |

The flask was shaken at room temperature for about 16 hours. A liquid sample was taken from each flask and analyzed by gas chromatography using a flame ionization detector (GC-FID). None of the hydrocarbons described in Table 2 were detected in any of the liquid samples after adsorption with the silica gels described in Table 1.

We claim:

1. A process for reducing hydrocarbon content of halosilanes, the process comprising: contacting a mixture comprising a halosilane and a hydrocarbon with silica gel, thereby reducing the hydrocarbon content of the mixture.

2. A process according to claim 1, where the mixture is a liquid when contacted with the silica gel.

3. A process according to claim 2, where the halosilane is a chlorosilane described by formula $R_aH_bSiCl_{4-a-b}$, a=0 to 3, b=0 to 3, a+b=0 to 3, and each R is a monovalent hydrocarbon radical comprising about one to 12 carbon atoms.

4. A process according to claim 3, where each R is independently selected from a group consisting of methyl, vinyl, and phenyl.

5. A process according to claim 1, where the process is run as a continuous process using multiple beds of silica gel and adsorption and desorption of the beds is staged to provide a continuous process.

6. A process according to claim 1, where the silica gel is of a regular-density type and has a surface area greater than about 500 $m^2/g$.

7. A process according to claim 1, where the silica gel comprises about 0.1 to 10 weight percent alumina.

8. A process according to claim 1, where the silica gel comprises about one to five weight percent alumina.

9. A process according to claim 1, where the silica gel is of a regular-density type and has a surface area greater than about 500 $m^2/g$ and contains about one to five weight percent alumina and the hydrocarbon comprises about one to 12 carbon atoms.

10. A process for reducing hydrocarbon content of chlorosilanes, the process comprising:

(A) contacting a mixture comprising a chlorosilane described by formula $R_aH_bSiCl_{4-a-b}$, where a=0 to 3, b=0 to 3, a+b=O to 3, and R is a monovalent hydrocarbon radical comprising about one to 12 carbon atoms, and a hydrocarbon comprising about one to 12 carbon atoms with silica gel, thereby recovering a chlorosilane reduced in hydrocarbon contend, (B) desorbing the silica gel to remove the hydrocarbon, and (C) reusing the silica gel as described in steps (A) and (B).

11. A process according to claim 10, where the mixture is a liquid when contacted with the silica gel.

12. A process according to claim 10, where desorbing the silica gel is accomplished by reducing the pressure below that pressure at which the mixture was contacted with the silica gel.

13. A process according to claim 10, where desorbing the silica gel is accomplished by raising the temperature of the process higher than that at which the mixture was contacted with the silica gel.

14. A process according to claim 10, where the silica gel is of a regular-density type and has a surface area greater than about 500 m$^2$/g.

15. A process according to claim 10, where the silica gel comprises about 0.1 to 10 weight percent alumina.

16. A process according to claim 10, where the silica gel comprises about one to five weight percent alumina.

17. A process according to claim 10, where the silica gel is of a regular-density type and has a surface area greater than about 500 m$^2$/g and contains about one to five weight percent alumina and the hydrocarbon comprises about one to 12 carbon atoms.

* * * * *